United States Patent
Nöcker et al.

(10) Patent No.: US 11,793,736 B2
(45) Date of Patent: Oct. 24, 2023

(54) DYEING COMPOSITION, METHOD, USE, AND KIT-OF-PARTS THEREOF

(71) Applicant: Kao Corporation, Tokyo (JP)

(72) Inventors: Bernd Nöcker, Darmstadt (DE); Steven Breakspear, Darmstadt (DE); Fariba Ghiasi, Darmstadt (DE); Anna Neu, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/634,749

(22) PCT Filed: Aug. 13, 2020

(86) PCT No.: PCT/EP2020/072744
§ 371 (c)(1),
(2) Date: Feb. 11, 2022

(87) PCT Pub. No.: WO2021/028530
PCT Pub. Date: Feb. 18, 2021

(65) Prior Publication Data
US 2022/0273536 A1    Sep. 1, 2022

(30) Foreign Application Priority Data
Aug. 14, 2019    (EP) .................................... 19191689

(51) Int. Cl.
| | | |
|---|---|---|
| *A61Q 5/10* | (2006.01) | |
| *A61K 8/34* | (2006.01) | |
| *A61K 8/04* | (2006.01) | |
| *A61K 8/22* | (2006.01) | |
| *A61K 8/41* | (2006.01) | |
| *A61K 8/43* | (2006.01) | |
| *A61K 8/73* | (2006.01) | |
| *A61K 8/81* | (2006.01) | |

(52) U.S. Cl.
CPC .............. *A61K 8/34* (2013.01); *A61K 8/042* (2013.01); *A61K 8/22* (2013.01); *A61K 8/411* (2013.01); *A61K 8/43* (2013.01); *A61K 8/731* (2013.01); *A61K 8/737* (2013.01); *A61K 8/8152* (2013.01); *A61Q 5/10* (2013.01); *A61K 2800/432* (2013.01); *A61K 2800/882* (2013.01)

(58) Field of Classification Search
CPC . A61K 8/34; A61K 8/042; A61K 8/22; A61K 8/411; A61K 8/43; A61K 8/731; A61K 8/737; A61K 8/8152; A61K 2800/432; A61K 2800/882; A61K 8/19; A61K 8/494; A61K 8/73; A61Q 5/10; A61Q 5/065
USPC ............................................................ 8/405
See application file for complete search history.

(56) References Cited

U.S. PATENT DOCUMENTS

| | | | |
|---|---|---|---|
| 2009/0049622 A1* | 2/2009 | Matsunaga | A61Q 5/10 558/405 |
| 2015/0328100 A1* | 11/2015 | Möhring | A61K 8/22 8/431 |
| 2017/0196791 A1 | 7/2017 | Nojiri | |
| 2018/0369103 A1* | 12/2018 | Owens | A61K 8/817 |
| 2020/0188262 A1 | 6/2020 | Nocker et al. | |

FOREIGN PATENT DOCUMENTS

| | | | |
|---|---|---|---|
| CN | 1248435 A | 3/2000 | |
| EP | 1 240 891 A2 | 9/2002 | |
| EP | 1 275 367 A1 | 1/2003 | |
| EP | 1 847 249 A1 | 10/2007 | |
| EP | 2 793 817 | 10/2014 | |
| EP | 2 793 817 A2 | 10/2014 | |
| EP | 2 883 530 A1 | 6/2015 | |
| EP | 2 883 531 A1 | 6/2015 | |
| EP | 3 153 154 A1 | 4/2017 | |
| EP | 3 342 464 A1 | 7/2018 | |
| EP | 3342464 A1 * | 7/2018 | ............ A61Q 5/10 |

OTHER PUBLICATIONS

International Search Report and Written Opinion dated Nov. 6. 2020 in PCT/EP2020/072744 filed Aug. 13, 2020. 11 pages.
Extended European Search Report dated Feb. 21, 2020 in European Patent Application No. 19191689.9 filled Aug. 14, 2019. 8 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

The present invention is directed to a dyeing composition, method, use and kit thereof, which improves dyeing using specific direct dyes. The inventive composition comprises benzyl alcohol, and a thickening polymer.

16 Claims, No Drawings

DYEING COMPOSITION, METHOD, USE, AND KIT-OF-PARTS THEREOF

FIELD OF THE INVENTION

The present invention is directed to a composition for dyeing of keratin fibers, a method of dyeing, and a use, and kit-of-parts for dyeing.

BACKGROUND OF THE INVENTION

A common approach to confer color to keratin fibers is the use of direct dyes. Such dyes have the advantage over oxidative dyes that the dyeing process leads to less damage of the keratin fibers. As a result, the appearance is cosmetically more attractive, especially after repeated dyeing cycles.

A general problem with direct dyes is their unsatisfactory dyeing property on keratin fibers, especially when intending to achieve dark color shades. The prior art has addressed these problems, but only partially delivered a satisfactory solution.

EP2793817 discloses bleaching/coloring compositions comprising direct dyes in anhydrous compositions, which are then mixed with an oxidizing composition and an oxidizable solvent. The present invention is directed to an alkaline non-oxidizing aqueous composition comprising certain direct dyes.

EP1240891 and EP1275367 disclose HC dyes of the present invention in combination with benzyl alcohol. However, the disclosures are silent on the presence of a thickening polymer.

EP1847249 discloses HC Blue 18 in aqueous dyeing compositions comprising benzyl alcohol. However, the composition of the disclosure is free of thickening polymers.

SUMMARY OF THE INVENTION

The first object of the present invention is a non-oxidizing aqueous composition for dyeing of keratin fibers, preferably human keratin fibers, more preferably human hair, having a pH in the range of 7 to 12 and comprising:
- one or more direct dye(s) selected from HC Red 18, HC Blue 18, and HC Yellow 16, and/or their mixtures,
- one or more thickening polymer(s) selected from non-ionic thickening polymers and/or anionic thickening polymers, and/or their mixtures,
- one or more alkalizing agent(s), and
- benzyl alcohol.

The second object of the present invention is a two-part dyeing composition for keratin fibers comprising as a first part the composition as defined above and as a second part an acidic aqueous composition comprising one or more guanidine compound(s) and/or its salt(s).

The third object of the present invention is a method for dyeing of keratin fibers, preferably human keratin fibers, more preferably human hair, comprising the steps of:
a) providing a first non-oxidizing aqueous composition as defined above,
b) providing a second aqueous acidic composition as defined above,
c) mixing the compositions of steps a) and b) to obtain a ready-to-use composition having a pH in the range of 7 to 12,
d) applying the ready-to-use composition onto keratin fibers and leaving it for a time period of 1 min to 60 min,
e) optionally rinsing the keratin fibers.

The fourth object of the present invention a method for dyeing of keratin fibers, preferably human keratin fibers, more preferably human hair, comprising the steps of:
f) applying the composition as defined above onto keratin fibers and leaving it for a time period in the range of 1 min to 60 min,
g) optionally rinsing the keratin fibers and optionally drying the keratin fibers.

The fifth object of the present invention is the use of a composition as defined in the above for dyeing of keratin fibers, preferably human keratin fibers, more preferably human hair.

The sixth object of the present invention is a kit-of-parts comprising a separately packed first composition as defined above and a separately packed second acidic aqueous composition as defined above, and optionally an oxidizing agent.

DETAILED DESCRIPTION OF THE INVENTION

Inventors of the present invention have unexpectedly found that an aqueous alkaline composition comprising certain direct dyes, an alkalizing agent, a thickening polymer, and benzyl alcohol provide for intensively dark color shades on keratin fibers, delivering brilliant and shiny color tones without conferring a large degree of damage to keratin fibers.

Composition for Dyeing of Keratin Fibers

The composition of the present invention is a non-oxidizing aqueous composition for dyeing of keratin fibers, preferably human keratin fibers, more preferably human hair, having a pH in the range of 7 to 12 and comprising:
- one or more direct dye(s) selected from HC Red 18, HC Blue 18, and HC Yellow 16, and/or their mixtures,
- one or more thickening polymer(s) selected from non-ionic thickening polymers and/or anionic thickening polymers, and/or their mixtures,
- one or more alkalizing agent(s), and
- benzyl alcohol.

The term 'non-oxidizing' is to be understood that the composition of the present invention comprises 1% by weight or less of bleaching compounds, preferably it is free of bleaching compounds.

Bleaching compounds are, for example, persalt(s) and/or peroxy salt(s) of alkaline or earth alkaline metals.

It is further preferred from the viewpoint of non-oxidizing that the composition of the present invention comprises 1% by weight or less of oxidative dye precursors and/or oxidative dye couplers, preferably it is free of oxidative dye precursors and/or oxidative dye couplers.

It is further preferred from the viewpoint of reducing damage to keratin fibers, preferably human keratin fibers, more preferably human hair, that the pH of the composition is in the range 8 to 11, more preferably in the range of 8.5 to 10.

Hair Direct Dyes

One or more direct dyes of the composition of the present invention are selected from HC Red 18, HC Blue 18, and HC Yellow 16, and/or their mixtures.

Preferably, the total concentration of direct dyes is 0.05% by weight or more, more preferably 0.1% by weight or more, further more preferably 0.2% by weight or more, calculated to the total weight of the composition, from the viewpoint of conferring sufficient color intensity to keratin fibers.

Preferably, the total concentration of direct dyes is 10% by weight or less, more preferably 5% by weight or less, further more preferably 3% by weight or less, calculated to the total weight of the composition, from the viewpoint of conferring sufficient color intensity to keratin fibers and cost of goods.

For attaining the above-mentioned effects, it is preferred that the total concentration of direct dyes is in the range of 0.05% to 10% by weight, more preferably 0.1% to 5% by weight, further more preferably 0.2% to 3% by weight, calculated to the total weight of the composition.

Thickening Polymers

The composition of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 8 and 10 having a viscosity of at least 5,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymers for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or less, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably 0.25% to 12% by weight, more preferably in the range of 0.5% to 10% by weight, calculated to the total weight of the composition.

Alkalizing Agents

The composition of the present invention comprises one or more alkalizing agent(s).

Suitable alkalizing agents are ammonia and/or its salt(s), guanidine and/or its salt(s), and/or organic alkyl and/or alkanol amines and/or their salt(s) according to the general structure

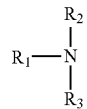

wherein $R_1$, $R_2$, and $R_3$ are independently selected from H, linear $C_1$-$C_6$ alkyl which may be substituted with one hydroxyl group, or branched $C_3$-$C_{12}$ alkyl or alkanol, wherein at least one of $R_1$, $R_2$, or $R_3$ is different from H, and/or their salts.

The organic alkyl and/or alkanol amine according to the structure above may be selected from mono- and/or diethanolamine, butyl ethanolamine, butyl diethanolamine, dibutyl ethanolamine, methylethanolamine, triethanolamine, N-lauryl diethanolamine, diisopropanolamine, dimethyl isopropanolamine, isopropanolamine, triisopropanolamine, isobutanolamine, aminomethyl propanol, monoethylamine, diethylamine, triethylamine. Equally suitable are salts of alkyl and/or alkanol amines with a counterion preferably selected from chloride and/or hydrogen chloride, nitrate, sulphate, phosphate, hydrogenphosphate, dihydrogenphosphate, citrate, acetate, sulphite, benzoate, salicylate.

It is preferred from the viewpoint of providing sufficient alkalinity that the alkalizing agent(s) is/are selected from ammonia and/or its salt(s), organic amine(s), alkanolamine(s), and/or their mixtures.

The most preferred alkalizing agent from the viewpoint of dyeing efficiency is ammonia and/or its salt(s).

Preferably, the total concentration of alkalizing agents is 1% by weight or more, more preferably 2% by weight or more, further more preferably 3% by weight or more, calculated to the total weight of the composition, from the viewpoint of providing sufficient alkalinity and dyeing efficiency.

Preferably, the total concentration of alkalizing agents is 20% by weight or less, more preferably 15% by weight or less, further more preferably 12% by weight or less, calculated to the total weight of the composition, from the viewpoint of providing low hair damage.

For attaining the above-mentioned effects, it is preferred that the total concentration of alkalizing agents is in the range of 1% to 20% by weight, more preferably 2% to 15% by weight, further more preferably 3% to 12% by weight, calculated to the total weight of the composition.

Benzyl Alcohol

The composition of the present invention comprises benzyl alcohol from the viewpoint of enhancing dye penetration into the hair fibers.

Preferably, the total concentration of benzyl alcohol is in the 1% by weight or more, more preferably 2% by weight or more, further more preferably 3% by weight or more, calculated to the total weight of the composition, from the viewpoint of dyeing efficiency.

Preferably, the total concentration of benzyl alcohol is in the 12% by weight or less, more preferably 10% by weight or less, further more preferably 8% by weight or less, calculated to the total weight of the composition, from the viewpoint of dyeing efficiency and cost of goods.

Preferably, for attaining the above-mentioned effects, the total concentration of benzyl alcohol is in the range of 1% to 12% by weight, more preferably 2% to 10% by weight, further more preferably 3% to 8% by weight, calculated to the total weight of the composition.

Viscosity

It is preferred from the viewpoint of enhancing dye uptake and preventing dripping from keratin fibers that the composition has a dynamic viscosity in the range of 10,000 mPa·s to 50,000 mPa·s, determined by cone-plate viscometry at 25° C., for example with a Brookfield viscometer and spindle #5. A sheer rate of 10 rpm is preferred.

Preferably, the viscosity of the composition of the present invention is 12,500 mPa·s or more, further more preferably 15,000 mPa·s or more, determined by cone-plate viscometry at 25° C., from the viewpoint of providing product viscosity.

Preferably, the viscosity of the composition of the present invention is 45,000 mPa·s or less, further more preferably 40,000 mPa·s or less, determined by cone-plate viscometry at 25° C. as explained above, from the viewpoint of providing product viscosity and easy application onto keratin fibers.

For attaining the above-mentioned effect, it is preferred that the viscosity is in the range of 12,500 mPa·s to 45,000 mPa·s, more preferably in the range of 15,000 mPa·s to 40,000 mPa·s, determined by cone-plate viscometry at 25° C., as explained above.

Product Forms

Suitably, the composition of the present invention is in any form that allows for easy application onto keratin fibers.

It is preferred from the viewpoint of cosmetic appearance that the composition is in gel form, more preferably it is in translucent gel form determined by observing the composition at 1 cm depth with the naked human eye.

In another aspect, the composition of the present invention is a gel-emulsion comprising one or more hydrophobic compounds, for example fatty alcohols, fatter acid esters, triglycerides, as well as mineral oil, and/or their mixtures. Suitable concentrations of hydrophobic compounds are in the range of 1% to 20% by weight, preferably 2% to 15% by weight, calculated to the total weight of the composition. For emulsification purposes, the composition preferably comprises one or more surfactant(s), which may be selected from the list of surfactants as laid out below.

Surfactants

In one aspect of the present invention, the composition comprises one or more surfactant(s).

Suitable surfactants are anionic, non-ionic, cationic, and/or zwitterionic/amphoteric surfactants, and/or their mixtures.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable examples are alkyl sulfate or preferably ethoxylated alkyl ether sulfate surfactant or mixtures thereof having an alkyl chain length of $C_{10}$ to $C_{22}$.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants. Suitable examples are cetrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of the composition, from the viewpoint of enhancing wettability of keratin fibers.

Two-Part Composition

The present invention is also directed to a two-part dyeing composition for keratin fibers comprising as a first part the composition as defined above and as a second part an acidic aqueous composition comprising one or more guanidine compound(s) and/or its salt(s).

Preferably, the second acidic aqueous composition has a pH in the range of 1 to 6, more preferably in the range of 2 to 5, still more preferably in the range of 2.5 to 4.5, from the viewpoint of cosmetic safety and mixability with the first composition.

Preferably, the guanidine compound(s) and/or its salt(s) is/are selected from guanidine, guanidine carbonate, guanidine hydrochloride, guanidine sulfate, and guanidine phosphate, and/or their mixtures, from the viewpoint of enhancing color intensity on keratin fibers. The most preferred guanidine compound(s) and/or its salt(s) is guanidine sulfate, from the viewpoint of enhancing color intensity on keratin fibers as well as enhancing wash fastness of the direct dyes.

It is preferred that the total concentration of the guanidine compound(s) and/or its salt(s) is 0.1% by weight or more, preferably 0.5% by weight or more, more preferably 1% by weight or more, calculated to the total weight of the composition, from the viewpoint of enhancing color intensity on keratin fibers.

It is preferred that the total concentration of the guanidine compound(s) and/or its salt(s) is 10% by weight or less, preferably 8% by weight or less, more preferably 6% by weight or less, calculated to the total weight of the composition, from the viewpoint of enhancing color intensity on keratin fibers and compound solubility.

For attaining the above-mentioned effects, it is preferred that the total concentration of the guanidine compound(s) and/or its salt(s) is in the range of 0.1% to 10% by weight, preferably in the range of 0.5% to 8% by weight, more preferably in the range of 1% to 6% by weight, calculated to the total weight of the composition.

Preferably, the second acidic composition may comprise one or more oxidizing agent(s), more preferably hydrogen peroxide, from the viewpoint of providing lightening to keratin fibers.

Suitable concentrations of one or more oxidizing agent(s), preferably hydrogen peroxide, in the second acidic composition is 1% by weight or more, preferably 2% by weight or more, more preferably 3% by weight or more, calculated to the total weight of the second acidic composition, form the viewpoint of providing lightening to keratin fibers.

Suitable concentrations of one or more oxidizing agent(s), preferably hydrogen peroxide, in the second acidic composition is 20% by weight or less, preferably 15% by weight or less, more preferably 12% by weight or less, calculated to the total weight of the second acidic composition, form the viewpoint of providing lightening to keratin fibers and cosmetic safety.

Suitable concentrations of one or more oxidizing agent(s), preferably hydrogen peroxide, in the second acidic composition is in the range of 1% to 20% by weight, preferably 2% to 15% by weight, more preferably 3% to 12% by weight, calculated to the total weight of the second acidic composition.

The second acidic aqueous composition preferably is an oil-in-water emulsion comprising one or more hydrophobic compound(s), form the viewpoint of cosmetic compatibility and providing conditioning effect. Suitable hydrophobic compounds are fatty alcohols, fatter acid esters, triglycerides, as well as mineral oil, and/or their mixtures. For emulsification purposes, the composition preferably comprises one or more surfactant which may be selected from the list of surfactants as laid out above.

Method for Dyeing

The present invention is also directed to a method for dyeing of keratin fibers, preferably human keratin fibers, more preferably human hair, comprising the steps of:
a) providing a first non-oxidizing aqueous composition as defined above,
b) providing a second aqueous acidic composition as defined above,
c) mixing the compositions of steps a) and b) to obtain a ready-to-use composition having a pH in the range of 7 to 12,
d) applying the ready-to-use composition onto keratin fibers and leaving it for a time period of 1 min to 60 min,
e) optionally rinsing the keratin fibers.

The aqueous composition of step b) preferably is an oil-in-water emulsion comprising one or more hydrophobic compound(s). Suitable hydrophobic compounds are fatty alcohols, fatter acid esters, triglycerides, as well as mineral oil, and/or their mixtures. For emulsification purposes, the composition preferably comprises one or more surfactant which may be selected from the list of surfactants as laid out above.

In one aspect of the present invention, the composition of step b) comprises one or more guanidine compound(s) and/or its/their salt(s), from the viewpoint of enhancing dyeing performance.

In case the keratin fibers are only desired to be colored, the composition of step b) is free of oxidizing agents.

In case the keratin fibers are desired to be lightened, the composition of step b) comprises one or more oxidizing agent(s).

For the latter purpose, the preferred oxidizing agent is hydrogen peroxide, and the concentrations are laid out as for the second acidic composition above, from the viewpoint of providing lightening to hair and from the viewpoint of cosmetic safety.

Compositions of steps a) and b) are mixed to yield a ready-to-use composition having a pH in the range of 7 to 12. Preferably, the pH is in the range 8 to 11, more preferably 8.5 to 10.5, from the viewpoint of hair damage and dyeing efficiency.

Suitably, the ready-to-use composition is left on keratin fibers for a time period of 1 min to 60 min. Preferably, it is left on keratin fibers for 2 min to 45 min, more preferably for 5 min to 30 min, from the viewpoint of process economy.

It is preferred from the viewpoint of cosmetic safety, that the ready-to-use composition is rinsed-off in step e).

However, if the composition of step b) is free of oxidizing agents, the ready-to-use composition does not have to be rinsed off in step e).

The invention is also directed to a method for dyeing of keratin fibers, preferably human keratin fibers, more preferably human hair, comprising the steps of:
f) applying the composition as defined above onto keratin fibers and leaving it for a time period in the range of 1 min to 60 min,
g) optionally rinsing the keratin fibers and optionally drying the keratin fibers.

It is preferred from the viewpoint of dyeing intensity and hair damage that the pH of the composition of step f) in the range of 7 to 12, more preferably in the range of 8 to 11, further more preferably in the range of 8.5 to 10.5.

Suitably the composition of step f) is left on keratin fibers for a time period of 1 min to 60 min. Preferably, it is left on keratin fibers for 2 min to 45 min, more preferably for 5 min to 30 min, from the viewpoint of process economy.

Use of Composition

The invention is also directed to a use of a composition as defined above for dyeing of keratin fibers, preferably human keratin fibers, more preferably human hair. As illustrated in the inventive examples, the composition of the present invention increases uptake of the direct dyes into keratin fibers.

Kit-of-Parts

The invention is also directed to a kit-of-parts comprising a separately packed first composition as defined above for the inventive composition and a separately packed aqueous second acidic composition, optionally comprising an oxidizing agent.

The second composition preferably is the composition as defined as the second acidic composition for two-part dyeing composition.

The oxidizing agent, if present in the second acidic composition, preferably is hydrogen peroxide.

The following examples are to illustrate the invention, but not to limit it.

EXAMPLES

The hair dyes were dissolved in water comprising ammonia solution. Then benzyl alcohol and thickening polymer, if present, were added under constant stirring. The pH was adjusted as a last step.

TABLE 1

|  | Ingredients | Inventive example 1 [% by weight] | Comparative example 1 [% by weight] | Comparative example 2 [% by weight] | Comparative example 3 [% by weight] |
|---|---|---|---|---|---|
| Compositions | HC Blue 18 | 0.25 | 0.25 | 0.25 | 0.25 |
|  | HC Red 18 | 0.25 | 0.25 | 0.25 | 0.25 |
|  | HC Yellow 16 | 0.25 | 0.25 | 0.25 | 0.25 |
|  | Ammonia (25% w/w) | 6.0 | 6.0 | 6.0 | 6.0 |
|  | Xanthan gum | 2.0 | — | 2.0 | — |
|  | Benzyl alcohol | 6.0 | 6.0 | — | — |
|  | NaOH/HCl | q.s. ad pH 9.0 | | | |
|  | Water | Ad 100.0 | | | |

TABLE 1-continued

|  | Ingredients | Inventive example 1 [% by weight] | Comparative example 1 [% by weight] | Comparative example 2 [% by weight] | Comparative example 3 [% by weight] |
|---|---|---|---|---|---|
| Data | L* | 16.43 | 16.83 | 17.87 | 21.68 |
|  | a* | 2.34 | 2.96 | 3.89 | 2.76 |
|  | b* | 1.79 | 2.52 | 4.45 | 9.05 |
|  | C* | 2.95 | 3.89 | 5.91 | 9.46 |
|  | h | 37.43 | 40.4 | 48.9 | 73.05 |

The dynamic viscosity of inventive composition 1 and comparative composition 2 was around 20,000 mPas, whereas the other two compositions had a dynamic viscosity in the range of 500 to 1,000 mPas.

Discussion of Results

L* values of the examples of table 1 illustrate that inventive example 1 and comparative example 1 had similar degrees of dye uptake, whereas the other two comparative compositions showed lower dye uptake. To achieve a dark color, a lower degree of L* is superior and indicates a color closer to black.

Inventive example 1 had the lowest C* of all examples. An ideal black colored hair has a C* value of 0. Thus, the lower the C* value, the closer the color to black. Inventive example 1 is therefore superior to the comparative examples.

Methods

Hair Dyeing Experiments

Caucasian blond hair streaks were obtained from volunteers and merged to yield 2 g of hair per bundle. The streaks were the shampooed with a commercially available shampoo under the brand name Goldwell Dualsenses Color Shampoo, thoroughly rinsed, and allowed to air-dry completely. After complete air-drying of the hair streaks, the hair color was measured by spectrophotometrical analysis with a Datacolor 45G CT instrument obtained from Datacolor Inc., Lawrenceville, NJ, USA. 5 measurements points on the hair streaks were averaged ($a_1$, $b_1$).

Then 1 g of the example compositions from above were applied onto the hair streaks, massaged for 1 min, and allowed to rest for 15 min. The streaks were then rinsed with lukewarm water for 1 min and blow-dried. The hair streaks were then combed through and color measurements were conducted at 5 different positions on the streak ($a_2$, $b_2$)

Based on the CIE*Lab color space results obtained by the measurements, C* and h values for color difference were calculated according to the following equations:

$$C^* = \sqrt{a^{*2} + b^{*2}}$$

$$h = \tan^{-1}\left(\frac{b^*}{a^*}\right)$$

Viscosity Measurements 50 g of the compositions from above were placed in a tall, thin, beaker and used for viscosity measurements in the Brookfield viscometer and spindle #5 at 25° C. at a shear rate of 10 rpm.

Measurements were carried out for 1 min and the measurement value for dynamic viscosity was taken after 1 min of shearing. An average of 3 measurements was reported.

TABLE 2

|  | Ingredients | Inv. ex. 2 | Inv. Ex. 3 | Inv. Ex. 4 | Inv. Ex. 5 | Inv. Ex. 6 | Inv. Ex. 7 | Inv. Ex 8 | Comp. Ex. 4 | Comp. Ex. 5 |
|---|---|---|---|---|---|---|---|---|---|---|
|  |  | % by weight [AM] | | | | | | | | |
| Compo- | HC Blue 18 | 0.25 | 0.25 | 0.25 | 0.25 | 0.25 | 0.25 | 0.1 | 0.25 | 0.25 |
| sitions | HC Red 18 | 0.25 | 0.25 | 0.25 | 0.25 | 0.25 | 0.25 | 0.1 | 0.25 | 0.25 |
|  | HC Yellow 16 | 0.25 | 0.25 | 0.25 | 0.25 | 0.25 | 0.25 | 0.1 | 0.25 | 0.25 |
|  | Ammonia (25% w/w) | 8.0 | 8.0 | 8.0 | 8.0 | 8.0 | — | 4.0 | 8.0 | 8.0 |
|  | Monoethanolamine | — | — | — | — | — | 7.2 | — | — | — |
|  | Xanthan gum | 2.0 | 0.25 | — | — | — | 2.0 | — | 2.0 | — |
|  | Hydroxyethylcellulose | — | — | — | 2.0 | — | — | — | — | — |
|  | Carbopol 980 | — | — | — | — | — | — | 2.0 | — | — |
|  | Hydroxyethyl Acrylate/Sodium Acryloyldimethyl Taurate Copolymer | — | — | 2.0 | — | — | — | — | — | — |
|  | Benzyl alcohol | 6.0 | 6.0 | 6.0 | 6.0 | 6.0 | 6.0 | 6.0 | — | — |
|  | NaOH/HCl |  |  | q.s. ad pH 10.0 |  |  |  | q.s. ad pH 9.0 | q.s. ad pH 10.0 |  |
|  | Water |  |  |  | Ad 100.0 |  |  |  |  |  |
| Data | L* | 17.58 | 17.59 | 18.36 | 17.16 | 18.08 | 17.95 | 19.72 | 18.00 | 18.34 |
|  | a* | 8.73 | 8.55 | 7.42 | 7.37 | 5.58 | 7.93 | 10.59 | 11.57 | 12.21 |
|  | b* | 0.40 | 0.51 | 0.22 | 0.71 | 0.23 | 0.89 | −1.12 | 2.67 | 2.64 |
|  | C* | 8.74 | 8.57 | 7.42 | 7.41 | 5.59 | 7.98 | 10.65 | 11.87 | 12.49 |
|  | h | 2.62 | 3.41 | 1.72 | 5.52 | 2.32 | 6.42 | 353.97 | 13.01 | 12.20 |

Discussion of Results

The experiments of table 2 were recorded at different pH values.

L* values of the examples of table 2 illustrate a similar picture to table 1, where the inventive examples showed similar dye uptake.

Inventive examples of table 2 had the lower C* in contrast to the comparative examples. An ideal black colored hair has a C* value of 0. Thus, the lower the C* value, the closer the color to black.

It is pointed out that a* and b* also indicated a visual color shift. The higher the a* value, the more red the hair appeared. The higher the b* value, the more yellow the hair streak appeared. Thus, lower values are highly desirable, because black hair customers do not desire their hair to appear in red or yellow tones.

Methods

The same methods as for the examples of table 1 were used.

The following examples are within the scope of the present invention.

Inventive Example 9

First part

|  | % by weight |
| --- | --- |
| HC Blue 18 | 0.1 |
| HC Yellow 16 | 0.08 |
| HC Red 18 | 0.05 |
| Monoethanolamine | 5.0 |
| Hydroxypropylxanthan gum | 0.5 |
| Benzyl alcohol | 3.0 |
| Propylene glycol | 3.0 |
| NaOH/HCl | ad pH 9.5 |
| Water | ad 100.0 |

Second acidic part

|  | % by weight |
| --- | --- |
| Guanidine sulfate | 3.0 |
| NaOH/HCl | ad pH 3.5 |
| Water | ad 100.0 |

The first and second acidic compositions are mixed in the weight ratio of 1:1. The second composition may additionally comprise hydrogen peroxide at a concentration range of 1% to 20% by weight, calculated to the total weight of the second acidic composition.

Inventive Example 10

First part

|  | % by weight |
| --- | --- |
| HC Blue 18 | 0.1 |
| HC Yellow 16 | 0.1 |
| HC Red 18 | 0.25 |
| Ammonia (24.5% active) | 8.0 |
| Xanthan gum | 4.0 |
| Hydroxyethyl cellulose | 0.5 |
| Benzyl alcohol | 6.0 |
| Mineral oil | 8.0 |
| Sodium lauryl sulfate | 1.5 |
| Ceteareth-30 | 1.0 |
| NaOH/HCl | ad pH 9.5 |
| Water | ad 100.0 |

Second acidic part

|  | % by weight |
| --- | --- |
| Guanidine sulfate | 3.0 |
| Guanidine chloride | 1.0 |

-continued

Second acidic part

|  | % by weight |
| --- | --- |
| NaOH/HCl | ad pH 2.5 |
| Water | ad 100.0 |

The first and second acidic compositions are mixed in the weight ratio of 1:1.

The second composition may additionally comprise hydrogen peroxide at a concentration range of 1% to 20% by weight, calculated to the total weight of the second acidic composition.

The invention claimed is:

1. A kit-of-parts, comprising:
    a separately packed first non-oxidizing aqueous composition having a pH in the range of 7 to 12 and comprising:
        one or more direct dye(s) which are at least one selected from the group consisting of HC Red 18, HC Blue 18, and HC Yellow 16,
        one or more thickening polymer(s) which are at least one selected from the group consisting of non-ionic thickening polymers and anionic thickening polymers,
        one or more alkalizing agent(s), and
        benzyl alcohol; and
    a separately packed second aqueous acidic composition optionally comprising an oxidizing agent.

2. The kit-of-parts according to claim 1, wherein the non-oxidizing aqueous composition comprises 1% by weight or less of bleaching compounds.

3. The kit-of-parts according to claim 1, wherein the non-oxidizing aqueous composition is free of bleaching compounds.

4. The kit-of-parts according to claim 1, wherein the non-oxidizing aqueous composition comprises 1% by weight or less of oxidative dye precursors and/or oxidative dye couplers.

5. The kit-of-parts according to claim 1, wherein the non-oxidizing aqueous composition is free of oxidative dye precursors and/or oxidative dye couplers.

6. The kit-of-parts according to claim 1, wherein the non-oxidizing aqueous composition has a dynamic viscosity in the range of 10,000 mPas to 50,000 mPas, determined by cone-plate viscometry at 25° C., with a Brookfield viscometer using spindle #5.

7. The kit-of-parts according to claim 1, wherein the total concentration of benzyl alcohol in the non-oxidizing aqueous composition is in the range of 1% to 12% by weight, calculated to the total weight of the non-oxidizing aqueous composition.

8. The kit-of-parts according to claim 1, wherein the non-ionic thickening polymers are cellulose-based polymers.

9. The kit-of-parts according to claim 1, wherein the one or more thickening polymer(s) are selected from anionic thickening polymers, and the anionic thickening polymers are at least one selected from the group consisting of naturally-based anionic polymers and synthetic anionic polymers.

10. The kit-of-parts according to claim 9, wherein the naturally-based anionic polymer(s) is/are at least one selected from the group consisting of xanthan gum, dehydroxanthan gum, hydroxypropylxanthan gum, and carboxymethyl cellulose.

11. The kit-of-parts according to claim 9, wherein the synthetic anionic polymer(s) is/are non-associative anionic polymers.

12. The kit-of-parts according to claim 1, wherein the total concentration of thickening polymers in the non-oxidizing aqueous composition is in the range of 0.1% to 15% by weight, calculated to the total weight of the non-oxidizing aqueous composition.

13. The kit-of-parts according to claim 1, wherein the alkalizing agent is selected from ammonia and/or its salt(s), organic alkyl or alkanol amine(s) and/or their salt(s), and/or their mixtures.

14. The kit-of-parts according to claim 1, wherein the total concentration of alkalizing agents is in the range of 1% to 20% by weight, calculated to the total weight of the non-oxidizing aqueous composition.

15. A two-part dyeing composition for keratin fibers, comprising:
    as a first part a non-oxidizing aqueous composition having a pH in the range of 7 to 12 and comprising:
        one or more direct dye(s) which are at least one selected from the group consisting of HC Red 18, HC Blue 18, and HC Yellow 16,
        one or more thickening polymer(s) which are at least one selected from the group consisting of non-ionic thickening polymers and anionic thickening polymers,
        one or more alkalizing agent(s), and
        benzyl alcohol; and
    as a second part an acidic aqueous composition comprising one or more guanidine compound(s) and/or its salt(s), and optionally hydrogen peroxide.

16. A method for dyeing of keratin fibers, the method comprising:
    a) providing a first non-oxidizing aqueous composition having a pH in the range of 7 to 12 and comprising:
        one or more direct dye(s) which are at least one selected from the group consisting of HC Red 18, HC Blue 18, and HC Yellow 16,
        one or more thickening polymer(s) which are at least one selected from the group consisting of non-ionic thickening polymers and anionic thickening polymers,
        one or more alkalizing agent(s), and
        benzyl alcohol,
    b) providing a second aqueous acidic composition comprising one or more guanidine compound(s) and/or its salt(s), and optionally hydrogen peroxide,
    c) mixing the compositions of a) and b) to obtain a ready-to-use composition having a pH in the range of 7 to 12,
    d) applying the ready-to-use composition onto keratin fibers and leaving it for a time period of 1 min to 60 min, and
    e) optionally rinsing the keratin fibers.

* * * * *